United States Patent [19]

Bank et al.

[11] 4,132,594

[45] Jan. 2, 1979

[54] GAS DIFFUSION LIQUID STORAGE BAG AND METHOD OF USE FOR STORING BLOOD

[75] Inventors: Herman Bank, Altadena; Edward L. Cleland, Duarte, both of Calif.

[73] Assignee: The United States of America as represented by the Administrator of the National Aeronautics and Space Administration, Washington, D.C.

[21] Appl. No.: 700,467

[22] Filed: Jun. 28, 1976

[51] Int. Cl.² .......................... A61M 1/03; A61J 1/00; B65D 81/24; B65D 81/00

[52] U.S. Cl. ...................... 195/1.8; 422/41; 422/48; 55/158; 128/214 D; 128/272; 150/1; 206/439; 210/DIG. 23

[58] Field of Search .................. 23/258.5 R, 258.5 M; 55/158; 210/DIG. 23; 206/69, 439; 128/214 D, 272, DIG. 24; 150/1, 52 E; 195/1.8; 21/2, 58

[56] References Cited

U.S. PATENT DOCUMENTS

| | | | |
|---|---|---|---|
| 3,010,536 | 11/1961 | Plurien et al. | 55/158 |
| 3,060,934 | 10/1962 | Claff et al. | 23/258.5 M |
| 3,424,218 | 1/1969 | Vanderby et al. | 128/272 X |
| 3,442,002 | 5/1969 | Geary et al. | 55/158 X |
| 3,445,321 | 5/1969 | Groves | 55/158 X |
| 3,489,647 | 1/1970 | Kolobow | 23/258.5 M X |
| 3,874,384 | 4/1975 | Deindoerfer et al. | 128/272 |
| 3,953,329 | 4/1976 | Updike | 195/1.8 X |

Primary Examiner—Barry S. Richman
Attorney, Agent, or Firm—Monte F. Mott; Wilfred Grifka; Robert Kinberg

[57] ABSTRACT

It has been found that the shelf life of stored whole blood may be doubled by adding a buffer which maintains a desired pH level. However, this buffer causes the generation of $CO_2$ which, if not removed at a controlled rate, causes the pH value of the blood to decrease, which shortens the useful life of the blood. This invention provides a blood storage bag which permits the $CO_2$ to be diffused out at a controlled rate into the atmosphere, thereby maintaining the desired pH value while providing a bag strong enough to permit handling thereof.

17 Claims, 5 Drawing Figures

GAS DIFFUSION LIQUID STORAGE BAG AND METHOD OF USE FOR STORING BLOOD

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to an improved apparatus for storing whole blood.

It has been found that the addition of $NaHCO_3$, as a buffer, to store whole blood maintains a desired pH level which is quite beneficial. It was shown, that with such a buffer, the blood can be adequately preserved with good viability for 42 days, and that the oxygen transport capability (as measured by 2, 3-DPG determination) is also maintained at levels substantially above those achieved by presently available media.

However, the buffer releases $CO_2$ during storage which, if not removed at a controlled rate, causes the pH value of the blood to change to a value which rapidly damages the blood.

Storage of the blood in the conventional blood bags, used for such storage, even though the buffer is added to the blood does not increase the storage life of the blood significantly because of the $CO_2$ released by the buffer. Materials to make a bag, other than the medically approved material presently used, which can pass $CO_2$ at a controlled rate and yet which is strong enough to withstand handling are either too expensive or not suitable for storing blood, as far as is known.

OBJECTS AND SUMMARY OF THE INVENTION

An object of this invention is the provision of a novel blood storage bag whereby buffered blood shelf life is increased.

Another object of this invention is the provision of a novel and useful blood bag which permits the escape of $CO_2$ from the blood stored in it and yet is sufficiently durable to enable handling and to withstand the pressure on its walls by the stored blood.

The foregoing and other objects of the invention are achieved with a blood bag which has a structure which is thin enough to pass $CO_2$ effectively, yet strong enough to withstand handling without being ruptured. The blood bag is made out of a medical grade plastic material, such as polyvinyl chloride (PVC). The bag is made with regions thin enough to permit a desired rate of diffusion therethrough of $CO_2$. It also has thick or otherwise sufficiently reinforced regions which provide handling strength for the bag.

DESCRIPTION OF THE EMBODIMENT OF THE INVENTION

Figure 1:
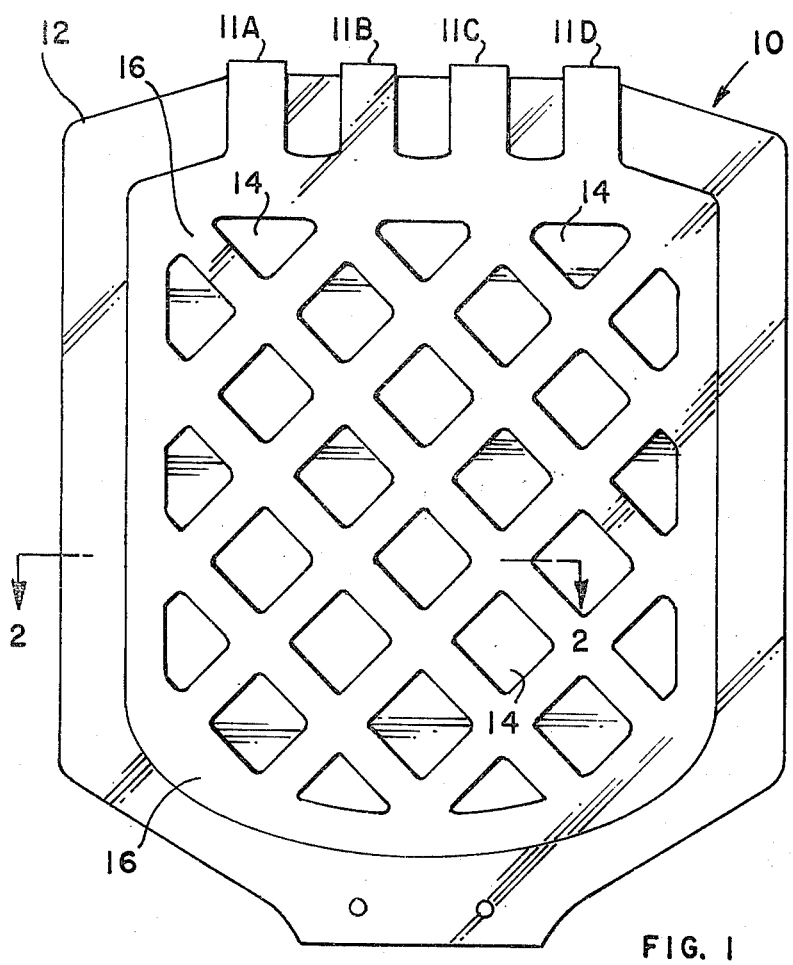
FIG. 1 is a view in elevation of a preferred embodiment of the invention.
Figure 2:
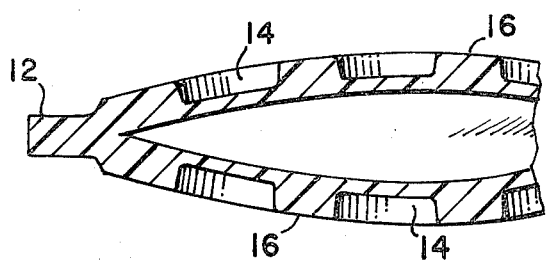
FIG. 2 is a cross-sectional view of FIG. 1 along the lines 2—2.

In FIG. 1, there may be seen a view in elevation of a container for blood. FIG. 2 is a cross-section along the lines 2—2. The container 10, is filled with blood through entrance pipes 11A, 11B, 11C, 11D. These entrance pipes are then sealed. These blood bags are usually made of a medical grade plastic material such as polyvinyl chloride (PVC), having essentially a uniform thickness on the order of 0.08 to 0.015 inch. It has been found that when sodium bicarbonate ($NaHCO_3$) is added to the blood, it maintains the desired pH level which has been proved beneficial in laboratory tests whereby the blood can be adequately preserved with great viability for 42 days, and oxygen transport capability (as measured by 2, 3-DPG determination) is maintained at levels substantially above those achieved by presently available media. However, the problem presented is that the blood bag containers do not permit the $CO_2$ which is generated as a result of the addition of the buffer to escape at an acceptable rate. This effectively reduces the benefits obtained by using the buffer.

The $CO_2$ removal must be at a rate such that the buffer can maintain the pH. If it escapes too slowly, as occurs in the present 15 mil thick PVC bags, the pH goes below pH 6. If $CO_2$ removal is too fast (as occurs with silicone bags), the pH goes to 9. It has been found that if the present medical grade PVC plastic bag, used for storing whole blood (or red blood cells), has its thickness sufficiently reduced then it becomes more permeable to the $CO_2$ generated within the bag, whereby it is released out into the atmosphere at a controlled higher rate, thereby the desired pH value of the whole blood may be maintained, while still shielding the whole blood from the atmosphere. However, when the bag is reduced to the thinness required for rendering it more permeable to $CO_2$, it effectively becomes so fragile that any handling of the bag, unless utmost care is taken, can cause a rupture of the bag. The bag must be handled since, for example, even in storage it is turned over periodically to produce a kind of stirring of the stored blood.

Accordingly, as can be seen in FIGS. 1 and 2, an arrangement is provided for making the bag thin enough over a sufficient area to attain the desired rate of passage therethrough of $CO_2$, while thick enough or strong enough, to enable the handling required, such as the indicated "turnovers", by giving the bag a waffle-type construction. That is, the conventional-sized bag, by way of example, has thin regions 14, having a thickness on the order of 1 to 6 mils, and thick regions 16, having a thickness on the order of 50 to 150 mils. The material of which the bag is constructed, in the end regions 12, is nominally also between 50 to 150 mils thick. The conventional sized storage blood bag is typically 7 inches long by 5 inches wide and stores 500 to 600 ml of fluid. Substantially 50% of the area of the bag constitutes the thin regions 14. The thick regions of the waffle grid, which incidentally extends on both sides of the bag, provide the necessary strength, abrasion resistance, etc. required to enable the bag to be handled without any problems. The thin regions provide the diffusion areas for the $CO_2$.

Figure 3:
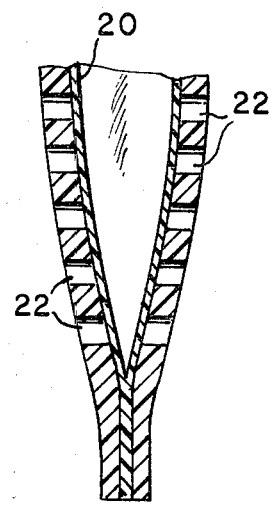
FIG. 3 is a cross-sectional view of another embodiment of the invention.

While the structure shown in FIGS. 1 and 2 can be made from a single sheet of plastic material, such as the medically approved PVC, other medically approved plastic materials may be used as well, in thicknesses that give a satisfactory $CO_2$ permeability rate. Also, the structure need not be made from a single, thick sheet of material. The bag may be made of two parts as shown in FIG. 3. An inner bag 20 which is made of medical grade plastic material, is placed within an outer bag 22. The bag 22 has surfaces which are perforated to enable the $CO_2$ passing through the inner bag to vent to the atmosphere. The outer bag may be of elastic material such as rubber or plastic or any other suitable material and is sized so that when the inner bag is filled, it will be in pressing contact against the outer bag. The outer bag supplies the necessary reinforcement to the inner bag so that it may be handled as required.

Figure 4:
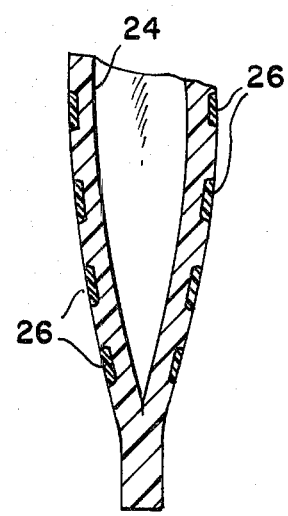
FIG. 4 is a cross-sectional view of still another embodiment of the invention.

FIG. 4 shows still another embodiment of the invention in cross section. Here the bag 24 is reinforced by embedding in the surface thereof a reinforcing mesh material 26, such as metallic foil (stainless steel) or plastic (nylon). The bag is made sufficiently thin over a large enough area to vent the $CO_2$ contained therein to the atmosphere at the rate required to maintain the pH of the stored fluid within the desired pH value.

Figure 5:
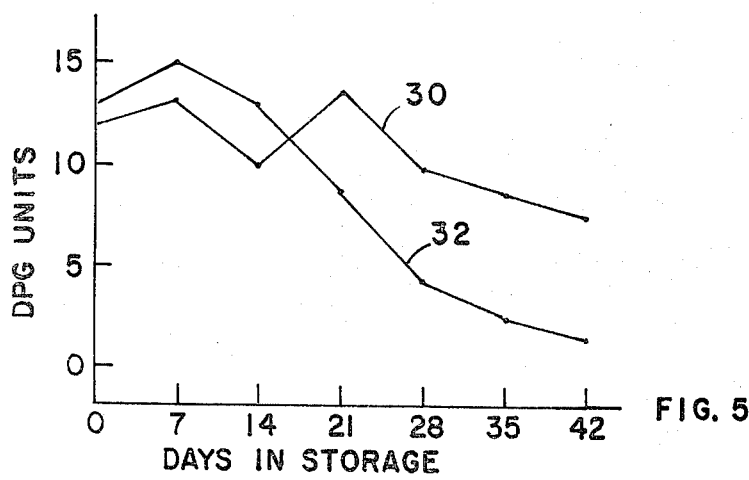
FIG. 5 is a graph comparing performance of the prior art with the present invention.

FIG. 5 is a graph illustrating the results obtained by testing the health of the blood, as measured in DPG units, which is kept in a conventional bag as compared with the health of the blood kept in a bag made in accordance with this invention. The ordinate of the graph is DPG units and the abscissa comprises days of storage. The curve 30 shows the data obtained by testing blood kept in a thin wall bag in accordance with this invention, as compared to the curve 32 indicating the health of the blood kept in the conventional bag. Blood at less than 8 DPG cannot be used. The chart shows that blood stored in a conventional bag may deteriorate to below 8 DPG in about 21 days, whereas blood stored under identical conditions, but in a bag in accordance with this invention, does not deteriorate to this value until approximately 40 days.

This high permeability blood bag concept can also be utilized to facilitate the diffusion of various gases or liquids into or out of the blood bag as desired (i.e., oxygen diffusion into the blood bag containing blood platelets). Furthermore, it is believed that the high permeability bag's design will result in a reduction of phthalate contamination of the blood compared to the contamination occurring in standard PVC blood bags.

Accordingly, there has been shown and described above a novel and useful bag for storing blood or other fluids where it is necessary to protect the fluid content of the bag, permit handling, while permitting the controlled diffusion of $CO_2$ from inside the bag to the atmosphere.

The embodiments of the invention in which an exclusive property or privilege is claimed are defined as follows:

1. A method of storing blood which has been treated with a selected compound to extend the useful life of the blood, said treatment resulting in the subsequent production of $CO_2$, the method comprising the steps of:
 providing a closeable plastic bag adapted to contain a preselected quantity of treated blood, the bag having first wall portions of a thickness chosen to enable $CO_2$ to diffuse through said portions at a selected predetermined rate so as to maintain the pH of said treated blood within a selected range, said bag having second wall portions for providing strength for said bag to withstand pressure applied thereto at least by the stored blood; and
 storing the treated blood in said bag.

2. A system for the storage of a liquid within a closed bag wherein a predetermined gas is formed, and for controlling a selected characteristic of said liquid, which is related to the content of said gas in said bag, said system comprising:
 a bag having semi-permeable wall means including thin wall means of preselected thickness for enabling said gas to diffuse through said thin wall means at a selected rate, to thereby control the selected characteristic of said liquid, said wall means including reinforcing means for enabling said bag to withstand pressure, wherein said reinforcing means comprises a spaced ribbing of the same material as the material of said thin wall means and which is integral therewith and of a thickness sufficient to reinforce said bag and the ratio of the surface area of said thin wall means to the total surface area of said bag is preselected to control the characteristic of said liquid by controlling the rate of diffusion of said gas through said thin wall means.

3. A system as recited in claim 2 wherein said reinforcing means are in excess of 50 mils thick.

4. A system as recited in claim 3 wherein the surface area that said thin wall means occupies is on the order of 50% of the total surface area of said wall means.

5. A system for storing whole blood or red blood cells which has been treated to extend its usable life, which treatment results in the production of $CO_2$ and requires the removal of $CO_2$ at a predetermined rate, so as to maintain the pH of the blood or the red blood cells within a selected range, said system comprising:
 a bag having semi-permeable wall means including thin wall means of preselected thickness for enabling $CO_2$ to diffuse through said wall means at a selected rate, said wall means including reinforcing means juxtaposed with said thin wall means for enabling said bag to withstand pressure, the ratio of the surface area of said thin wall means, which do not include said reinforcing means, to the total surface area of said wall means being selected to control the rate of diffusion of the $CO_2$ through said thin wall means so that the pH of the blood or the red blood cells in said bag is maintained within said selected range.

6. A system as recited in claim 5 wherein said thin wall means of said bag form a first closed bag and said reinforcing means of said bag constitute a second open mesh bag into which said first bag is inserted, said second open mesh bag being made of elastic material and being sized to apply pressure to said first bag when it is filled with said blood or red blood cells.

7. A system as described in claim 5 wherein the surface area that said thin wall means occupies is on the order of 50% of the total surface area of said wall means.

8. A system as recited in claim 5 wherein said reinforcing means comprises a mesh of material embedded in the surface of said thin wall means.

9. A system as recited in claim 8 wherein said mesh of material is nylon.

10. A system as recited in claim 8 wherein said mesh of material is a metallic foil.

11. A system as described in claim 5 wherein at least said thin wall means are made of medical grade material.

12. A system as described in claim 11 wherein said thin wall means and said reinforcing means are of the same material with the thickness of said thin wall means being on the order of 1 to 6 mils and the thickness of said reinforcing means being not less than 50 mils.

13. A system as described in claim 12 wherein the surface area that said thin wall means occupies is on the order of 50% of the total surface area of said wall means.

14. A system as described in claim 11 wherein the thickness of said thin wall means is on the order of 1 to 6 mils.

15. A system as described in claim 14 wherein the surface area that said thin wall means occupies is on the order of 50% of the total surface area of said wall means.

16. A system as described in claim 14 wherein said reinforcing means are in excess of 50 mils thick.

17. A system as described in claim 16 wherein the surface area that said thin wall means occupies is on the order of 50% of the total surface area of said wall means.

* * * * *